United States Patent [19]
Radisson

[11] Patent Number: 5,272,266
[45] Date of Patent: Dec. 21, 1993

[54] VINYLSULPHONYLPRISTINAMYCIN AND ITS PREPARATION

[75] Inventor: Xavier Radisson, Lyons, France
[73] Assignee: Rhone-Poulenc Rorer S.A., France
[21] Appl. No.: 961,923
[22] PCT Filed: Jul. 15, 1991
[86] PCT No.: PCT/FR91/00581
  § 371 Date: Jan. 4, 1993
  § 102(e) Date: Jan. 4, 1993
[87] PCT Pub. No.: WO92/01708
  PCT Pub. Date: Feb. 6, 1992

[30] Foreign Application Priority Data
Jul. 16, 1990 [FR] France ................ 90 09035

[51] Int. Cl.$^5$ ............... C07D 498/14; A61K 31/42
[52] U.S. Cl. .................................. 540/456
[58] Field of Search .......................... 540/456

[56] References Cited
FOREIGN PATENT DOCUMENTS
135410 3/1985 European Pat. Off. .......... 540/456
252720 1/1988 European Pat. Off. .......... 540/456

Primary Examiner—Robert T. Bond
Attorney, Agent, or Firm—Morgan & Finnegan

[57] ABSTRACT

This invention relates to vinylsulphonylpristinamycin, its preparation and use as an intermediate.

7 Claims, No Drawings

VINYLSULPHONYLPRISTINAMYCIN AND ITS PREPARATION

FIELD OF THE INVENTION

The present invention relates to a new pristinamycin $II_B$ derivative of formula:

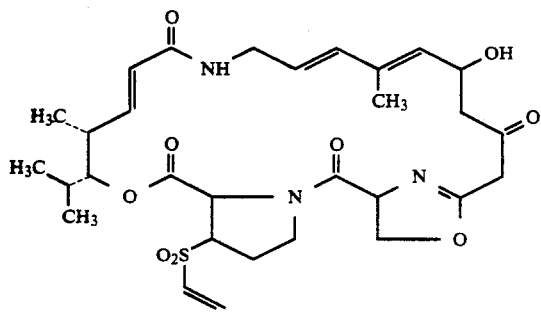

as well as to their preparation.

BACKGROUND OF THE INVENTION

Pristinamycin $II_B$ derivatives have been described previously in American Patents U.S. Pat. No. 4,590,004 and U.S. Pat. No. 4,668,669. These products have the property of synergizing the antimicrobial activity of pristinamycin $I_A$.

Vinyl sulphones are useful products as synthesis intermediates, especially in carrying out Michael reactions. Their preparation is generally performed in several steps, among which an oxidation step and often the isolation of an intermediate sulphone take place, since the preparation is performed in most cases by proceeding via a thiol.

DESCRIPTION OF THE INVENTION

It is found that the vinyl sulphone of formula (I) could be obtained in high yield in one oxidation step, after introducing the sulphur bearing an appropriate functional group at the β-position.

According to the invention, the vinyl sulphone derived from pristinamycin $II_B$ may be prepared by oxidation of a 26-[2-(dialkylamino)ethylthio]pristinamycin $II_B$ of general formula:

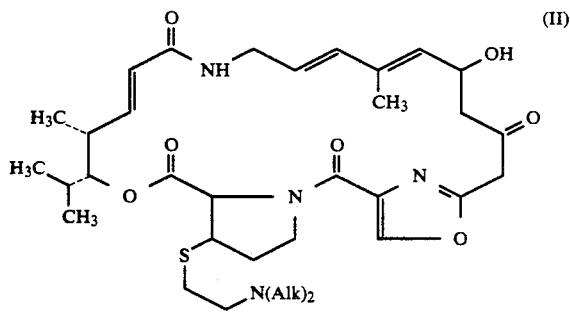

in which Alk is an alkyl radical containing 1 to 4 carbon atoms in a straight or branched chain, with 4 to 6 equivalents of hydrogen peroxide in the presence of a catalyst such as ammonium molybdate or sodium tungstate.

This new technique has the advantage of being very gentle and very specific. It may hence be applied to delicate molecules containing a large number of functions capable of being adversely affected by the reaction, as is the case with the component II of pristinamycin.

The reaction is performed in an alcohol, such as, for example, ethanol, methanol or isopropanol, at a temperature of between $-25°$ and $+25°$ C. The quantity of catalyst, expressed in moles % is introduced in the proportion of 1 to 7 % of the starting thioether.

It is essential to work in the presence of a large excess of hydrogen peroxide: in the proportion of 4 to 6 equivalents per mole of sulphide employed in the reaction. Preferably, the reaction is performed in the presence of 5 equivalents of oxidizing agent.

In the case of a reaction catalyzed by sodium tungstate, it is understood that the reaction may be carried out at low temperature, but it is necessary for the last part of the reaction to be carried out at a temperature not below 0° C.

Another advantage of the new process according to the invention is that of enabling vinyl sulphones derived from pristinamycin $II_B$ to be obtained in high yields and without subsequent purification.

The 26-[2-(dialkylamino)ethylthio]pristinamycin $II_B$ of general formula (II) may be obtained as described in U.S. Pat. No. 4,590,004.

The vinyl sulphone according to the invention is useful as an intermediate for the preparation of pristinamycin $II_B$ derivatives of general formula:

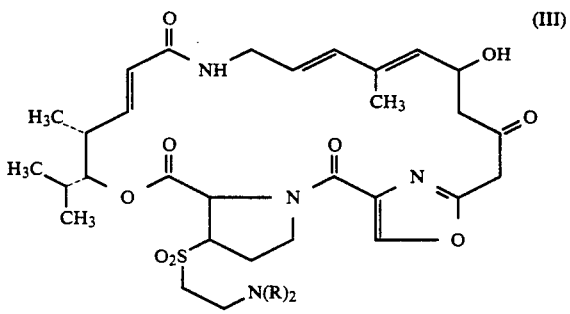

in which R is a linear or branched alkyl radical containing 1 to 10 carbon atoms, by the action of the amine of general formula:

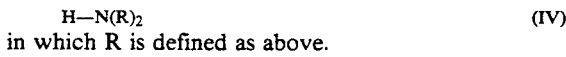

in which R is defined as above.

The reaction is generally performed in a chlorinated solvent such as, for example, methylene chloride, at a temperature of between 0° and 25° C.

The pristinamycin derivatives of general formula (III) are especially advantageous products which are described in U.S. Pat. No. 4,668,669 for their antibacterial activity and their synergistic action on the antibacterial activity of natural pristinamycin $I_A$, virginiamycin S and soluble derivatives of these products.

EXAMPLE

The examples which follow, given without implied limitation, illustrate the present invention.

EXAMPLE 1

65.9 g (0.1 mol) of 26-[2-(diethylamino)thio]pristinamycin $II_B$ are placed in 400 cm$^3$ of ethanol and cooled to $-20°$ C. The oxidizing agent (ammonium molybdate: 8.65 g, 7 % +hydrogen peroxide (30 %): 51.5 cm$^3$, 5 eq.) is added in the course of 20 minutes at between $-20°$ and $-15°$ C. and stirring is continued for 40 minutes at $-20°$ C. In the course of 6 minutes, 100 cm$^3$ of water are poured in, the cooling bath is removed and the solution (0° C.) is extracted with 500 cm$^3$ of methylene chloride. The organic phase is washed with 4 times 100 cm$^3$ of water. An HPLC assay of the organic phase, gives, at this stage, a TY=90%.

The organic solution is stirred for 15 minutes with 100 cm$^3$ of 1N sulphuric acid solution, then washed with 3 times 50 cm$^3$ of water, dried over sodium sulphate and concentrated to dryness. A yellow solid is obtained in a weight yield of 88.8 % and a content of 26-(vinylsulphonyl)pristinamycin II$_B$ of 72 % (HPLC), equivalent to a true yield of isolated product: TY=63 %.

EXAMPLE 2

As in Example 1, 3.29 g (5 mmol) of 26-[2-(diethylamino)-ethylthio]pristinamycin II$_B$ are placed in 20 cm$^3$ of ethanol and cooled to $-20°$ C. The oxidizing solution (ammonium molybdate: 0.346 g, 5.6 % + hydrogen peroxide (30 %): 2.05 cm$^3$, 4 eq.) is added in the course of 5 minutes while the temperature is maintained at between $-15°$ C. and $-20°$ C. The reaction mixture is stirred for 1 hour at this temperature and then 15 minutes at between 0° and 5° C. to yield 26-(vinylsulphonyl)pristinamycin II$_B$ in a 67 % yield.

EXAMPLE 3

1 g (1.51 mmol) of 26-[2-(diethylamino)ethylthio]pristinamycin II$_B$ is stirred in 6.1 cm$^3$ of ethanol and cooled to $-20°$ C. The oxidizing agent [sodium tungstate dihydrate: 5 mg (1 mol %) + hydrogen peroxide (30 %): 0.856 g, 5 equivalents] is added in the course of 2 minutes at $-20°$ C. After 1 hour at $-20°$ C., the reaction mixture is brought back to $+22°$ C. and, after 2 hours, a true yield of 26-(vinylsulphonyl)pristinamycin II$_B$, TY=45 % (HPLC assay), is obtained.

EXAMPLE OF USE

Diethylamine (0.0517 g, 0.704 mM), diluted with methylene chloride to a total volume of 0.5 cm$^3$, is added in the course of 20 minutes at approximately 20° C. to a solution of 26-(vinylsulphonyl)pristinamycin II$_B$ (0.5 g, content 87 %, 0.704 mM) in 5 cm$^3$ of methylene chloride. The mixture is stirred for 1 hour 15 minutes and then concentrated to dryness in a rotary evaporator for 25 minutes. A solid (total mass 0.531 g) is thereby obtained, containing 26-[2-(diethylamino)ethylsulphonyl]pristinamycin II$_B$, content 59.5 % (TY=65 %) and the starting 26-(vinylsulphonyl)pristinamycin II$_B$, 5.1 %. (Degree of conversion DC=94 %; TotY=69 %).

Although the invention has been described in conjunction with specific embodiments, it is evident that many alternatives and variations will be apparent to those skilled in the art in light of the foregoing description. Accordingly, the invention is intended to embrace all of the alternatives and variations that fall within the spirit and scope of the appended claims. The above references are hereby incorporated by reference.

I claim:

1. Pristinamycin II$_B$ derivative of formula:

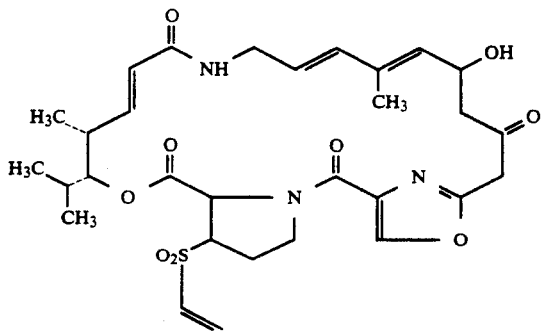

2. Process for preparing a vinyl sulphone according to claim 1, wherein a 26-[2-(dialkylamino)-ethylthio]-pristinamycin II$_B$ of formula:

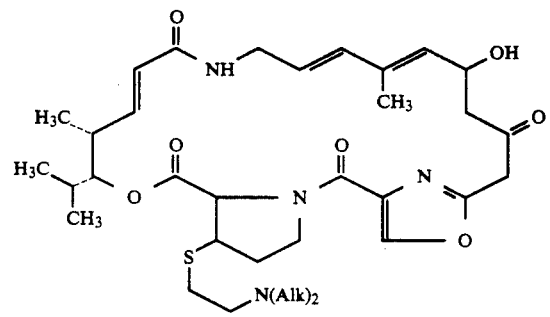

in which Alk is an alkyl radical containing 1 to 4 carbon atoms in a straight or branched chain, is oxidized with 4 to 6 equivalents of hydrogen peroxide in the presence of a catalyst such as ammonium molybdate or sodium tungstate.

3. Process according to claim 2, wherein the catalyst is introduced in the proportion of 1 to 7 mol % relative to the starting thioether.

4. Process according to claim 2, wherein the reaction is performed in the presence of ammonium molybdate.

5. Process according to claim 2, wherein the reaction is performed in the presence of sodium tungstate at a temperature in the last part of the reaction above 0° C.

6. Process according to claim 2, wherein the reaction is performed in ethanol, methanol or isopropanol.

7. Method for the preparation of pristinamycin II$_B$ derivatives of formula:

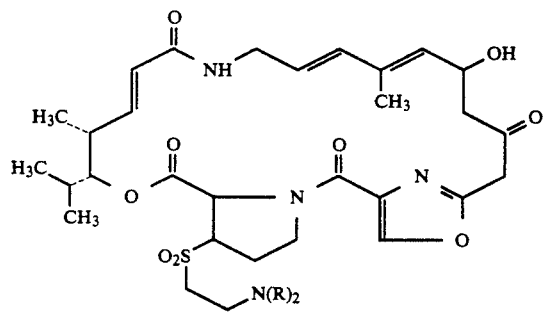

in which R is a liner or branched alkyl radical containing 1 to 10 carbon atoms, by the action of an amine of formula:

$$H-N(R)_2$$

in which R is defined as above comprising using a vinyl sulphone according to claim 1.

* * * * *